United States Patent [19]

Wesley

[11] Patent Number: 4,458,153
[45] Date of Patent: Jul. 3, 1984

[54] ORGANISM DESTRUCTION BY ELECTROHYDRAULIC DISCHARGE WITHIN A PULSED MAGNETIC FIELD ENVELOPE

[76] Inventor: Richard H. Wesley, 19511 Ricelake La., Houston, Tex. 77084

[21] Appl. No.: 416,946

[22] Filed: Sep. 13, 1982

[51] Int. Cl.³ .................................................. G01N 21/01
[52] U.S. Cl. ..................................... 250/435; 250/436; 422/22
[58] Field of Search .................. 250/455.1, 432, 435, 250/436, 434; 422/22, 23; 210/222, 138, 243

[56] References Cited

U.S. PATENT DOCUMENTS

| | | | |
|---|---|---|---|
| 3,345,594 | 10/1967 | Vermeiren | 210/222 |
| 3,366,564 | 1/1968 | Allen | 422/22 |
| 3,522,167 | 7/1970 | Allen | 422/22 |
| 3,600,126 | 8/1971 | Hellund | 422/23 |
| 4,066,544 | 1/1978 | Stark | 422/22 |

Primary Examiner—Bruce C. Anderson
Attorney, Agent, or Firm—Gunn, Lee & Jackson

[57] ABSTRACT

Method of and apparatus for killing microorganisms in a substance, characterized by the step of conjointly generating a magnetic field and an electrohydraulic discharge and subjecting every differential volume of the substance to the combined physical magnetic field and the electrohydraulic discharge of lethal intensity at least once. The physical magnetic field is at least of a sufficient intensity to contain and direct the electrohydraulic discharge and preferably, is itself of lethal intensity. The pulsed magnetic field and the electrohydraulic discharge are repeated at a frequency proportional to the rate of flow of the substance through a volumetric region into which the magnetic field is passed and within which the electrohydraulic discharge electrodes are located. Also discussed are preferred embodiments, in which the substance is a liquid-like substance, such as sewage, chemical waste, liquid mining material, etc.; and preferred apparatus; and preferred modes of operation such as continuous, batch, and modified batch-continuous.

37 Claims, 9 Drawing Figures

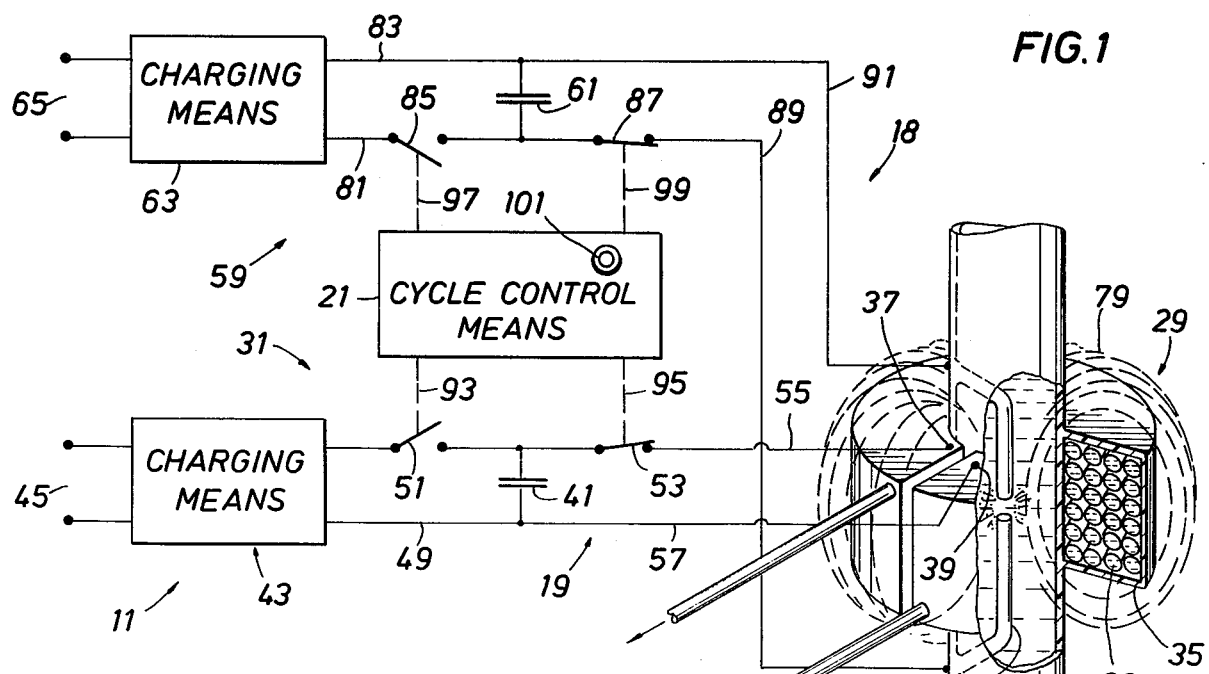
FIG.1
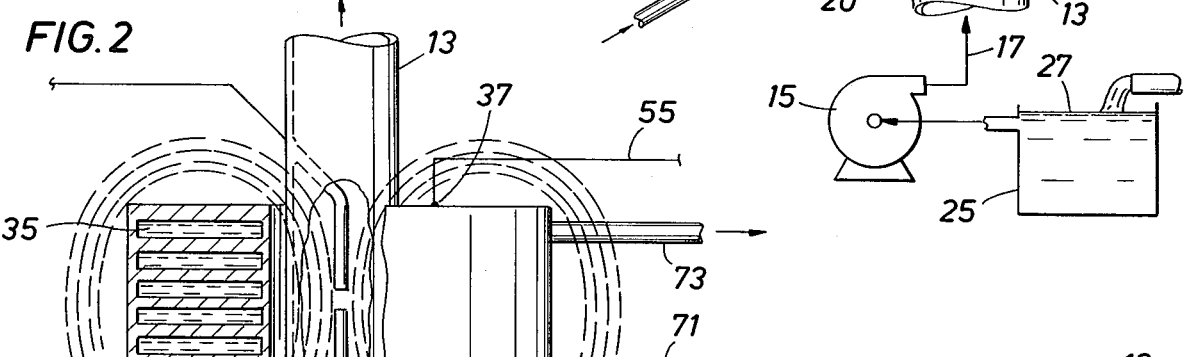
FIG.2
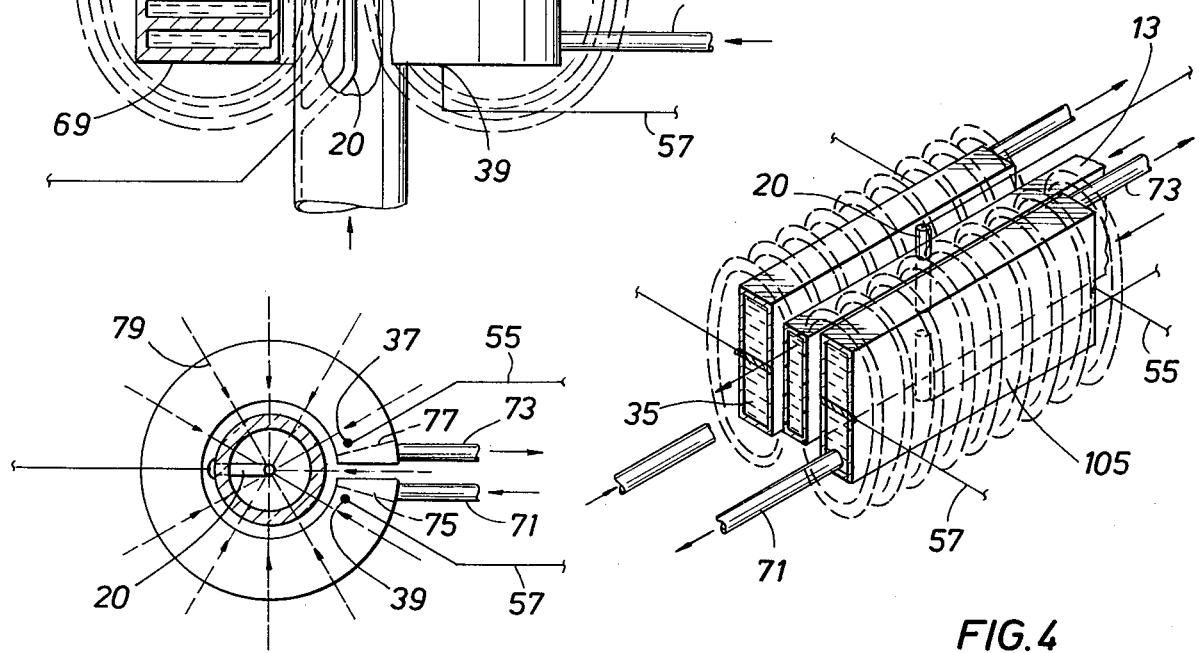
FIG.3
FIG.4

ORGANISM DESTRUCTION BY ELECTROHYDRAULIC DISCHARGE WITHIN A PULSED MAGNETIC FIELD ENVELOPE

BACKGROUND OF THE INVENTION

1. Field of the Invention

This invention relates to a process for treating a substance containing microorganisms to render the microorganisms inactive. More particularly, this invention relates to process and apparatus for treating liquid-like substances such as sewage, chemical waste, liquid mining material, etc., to kill the microorganisms therein.

2. Description of the Prior Art

Numerous methods and apparatus are known in the prior art for treating materials to render inactive the microorganisms therein. In addition to the well known, but time-consuming processes such as pasteurization, bacterial action, and the like, it is known in the prior art to employ high frequency electromagnetic wave energy to irradiate a liquid for rendering inactive the microorganisms therein. It is also known to employ pulsed electrical discharge between electrodes to effect neutralization of the microorganisms in the liquid in which the electrodes are disposed. Such electrical discharge between electrodes is commonly referred to as electrohydraulic discharge. One of the difficulties of the electrohydraulic discharge has been the containment of the relatively tremendous localized pressures developed by the electrohydraulic discharge. That is, either the electrohydraulic discharge must be on a very small scale such as between closely adjacent electrodes for purifying lines and the like, or if vessels of appreciable size were employed to enclose the liquid to be treated, the vessels had to be structurally strong, and hence expensive, to contain the force generated by the electrohydraulic discharge of an intensity lethal to the microorganisms. The prior art electrohydraulic methods required that the strong vessel be closed and hence required a batch process and was not susceptible to a wide variety of processes such as the continuous or modified batch-continuous operation.

One of the particular problems that has bothered the prior art apparatus employing electrohydraulic discharges has been the problems with the electrohydraulic electrodes. Since the electrodes were rapidly eroded, they were deformed by the shock wave produced by the electrohydraulic discharge, or were blown from the region where the electrohydraulic discharge was effected. Thus, it can be seen that the prior art methods and apparatus have not been completely satisfactory in effecting treatment of large volumes of material such as the effluent to or from a sewage plant.

It is a primary object of this invention to provide method and apparatus for treating a substance to kill the microorganisms therein that obviate the disadvantages of the prior art methods and apparatus.

It is a particular object of this invention to provide apparatus for treating a liquid-like substance to kill microorganisms therein that is operable in either continuous, batch, or batch-continuous processes and that avoids the necessity for closed, thick-walled vessels with high structural strength to contain the electrohydraulic discharge employed in the treatment.

In this regard, it is also a particular object of the invention to provide a preferred form of electrohydraulic electrodes that minimizes deletrious erosion of the electrodes and alleviates the problem with deforming or blowing the electrodes from the region wherein the electrohydraulic discharge is effected, and to provide preferred magnetic field generating structure for effecting the desired shape of the magnetic field for containing and directing the electrohydraulic discharge.

This invention employs both the electrohydraulic discharge and the magnetic field and, hence, may be employed to treat a wide variety of substances, particularly where the magnetic field is itself lethal to the microorganisms contained therein. Ordinarily, however, best results are obtained from the electrohydraulic discharge if the substance is in the form of a liquid-like substance which can be flowed through the volumetric region with which the electrohydraulic discharge is associated and within the magnetic field generating structure. The term "liquid-like" is used herein to mean any substance that behaves like a liquid, including but not limited to liquids, liquids having solids or semisolids therein, slurries, and suspensions. The invention may be employed in a wide variety of fields of technology, including the treatment of juices and food slurries, the sterilization of waste, and extraction of minerals from brines, biological or chemical slurries and the like. It will be discussed herein, however, in a specific aspect of treating sewage for purposes of simplicity.

Liquid-like substances are preferable since they are readily flowed through a volumetric region in association with the electrohydraulic discharge electrodes and within the magnetic field. Also, the shock wave of the electrohydraulic discharge becomes steeper and more nearly approaches infinity in slope in a liquid, particularly where the liquid has some electrical conductivity. The invention can improve the extraction of elements from solution as originally mentioned in U.S. Pat. No. 3,220,873, issued Nov. 30, 1965. This technique will begin to cause a separation of material due to specific gravity and magnetic susceptibility. Also the "in line" electrodes are used to establish a continuous closed system flow. Firing of the ignitrons will be in a sequence based upon flow velocity and so that each volume of fluid will be treated more than once at a predetermined energy level.

BRIEF DESCRIPTION OF THE DRAWINGS

So that the manner in which the above cited features, advantages and objects of the invention, as well as others which will become apparent, are attained and can be understood in detail, a more particular description of the invention, briefly summarized above, may be had by reference to the embodiments thereof illustrated in the appended drawings, which drawings form a part of this specification. It is to be noted, however, that the appended drawings illustrate only typical embodiments of the invention and are not to be considered limiting of its scope, for the invention may admit to other equally effective embodiments.

In the Drawings

FIG. 1 is a schematic illustration, partly in section, of one embodiment of this invention.

FIG. 2 is a side elevational view, partly in section, illustrating another embodiment of the magnetic field generating structure that may be employed in this invention.

FIG. 3 is a top plan view of the embodiment of FIG. 2.

FIG. 4 is a partial isometric view of a different type of magnetic field generating structure employed in another embodiment of this invention.

DETAILED DESCRIPTION OF THE PREFERRED EMBODIMENT

Figure 6:
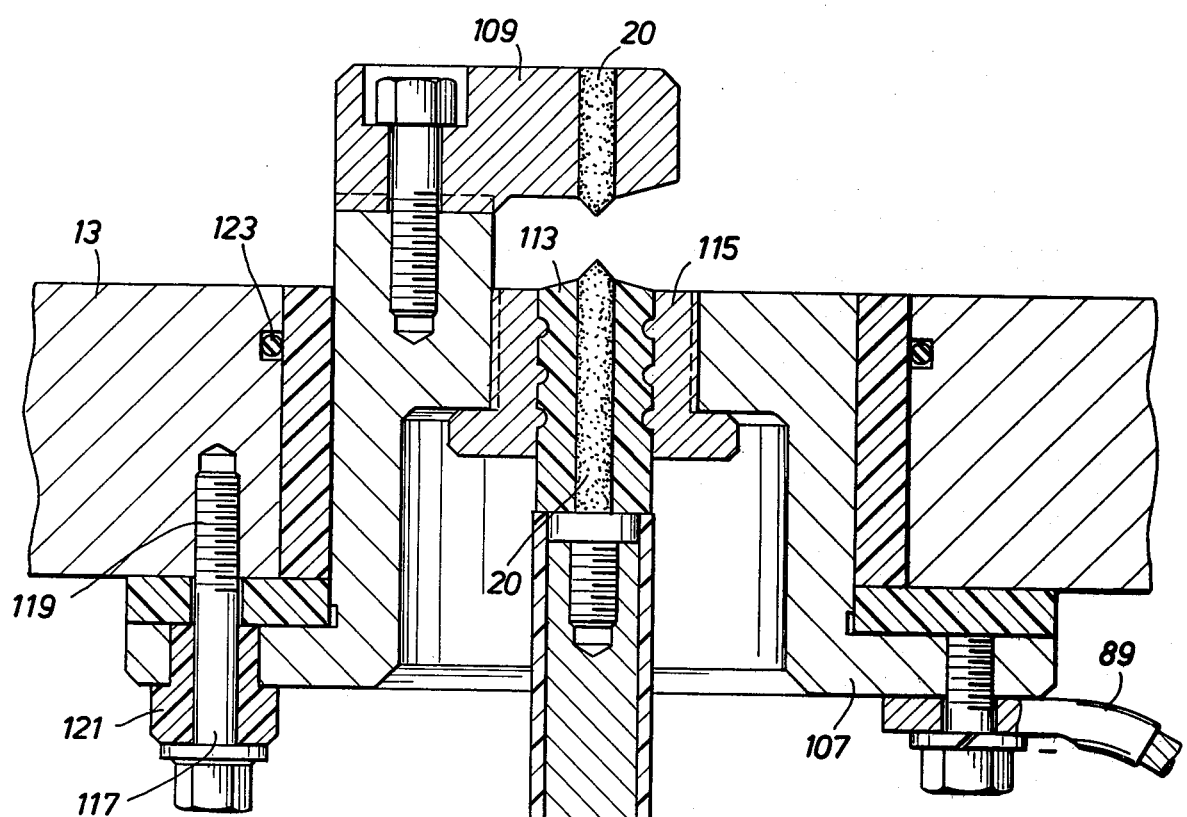
FIG. 6 is a side sectional view of an electrode useful in an embodiment of this invention.

Referring now to the drawings and first to FIG. 1, the apparatus 11 includes a nonmagnetic, conductive means illustrated by flow conduit 13, defining a volumetric region for receiving the substance to be treated. The term "nonconductive" is employed herein to mean electrically nonconductive. A flow means, illustrated by pump means 15, and conduit 17 are connected with the flow conduit 13 for passing the liquid-like substance through the volumetric region defined by the flow conduit 13. The usual flow control valves may be employed in addition to pump means 15 to effect the desired rate of flow.

An electrohydraulic discharge generating means 18 include a plurality of electrodes 20 communicating with the liquid-like substance so as to generate an electrohydraulic discharge within the volumetric region defined within flow conduit 13 and pass an electrohydraulic shock wave through the liquid-like substance therein. The electrohydraulic discharge generating means 18 must be capable of generating an electrohydraulic discharge of an intensity sufficient to kill the microorganisms in the liquid-like substance being flowed through flow conduit 13 and about electrodes 20.

A magnetic field generating means 19 is disposed adjacent the nonmagnetic, nonconductive portion of flow conduit 13 so as to be able to pass a physical magnetic field into the volumetric region defined therein. The magnetic field generating means 19 must be capable of generating a physical magnetic field of an intensity sufficient to contain and direct the electrohydraulic discharge. Preferably, the physical magnetic field is of an intensity sufficient to also be lethal with respect to the microorganisms contained in the liquid-like substance. Advantageously, a pulsed magnetic field is employed. The pulse magnetic field has a gradient through the liquid-like substance that also has an intensity sufficient to contain and direct the electrohydraulic discharge, and preferably, that is lethal to the microorganisms contained within the substance.

Apparatus 11 includes a cycle control means 21 that is connected with the electrohydraulic discharge generating means 18 and with the magnetic field generating means 19, for conjointly effecting the generation of the physical magnetic field and the electrohydraulic discharge therein. The cycle control means 21 effects the respective generation of the magnetic fields and the electrohydraulic discharges at a frequency great enough to ensure that every differential volume of the liquid-like substance is subjected to at least one electrohydraulic discharge of lethal intensity. Preferably, the cycle control means 21 effects initiation of the physical magnetic field by the magnetic field generating means 19 to start a magnetic envelope that will help to contain the electrohydraulic discharge, as well as contribute its own unique and not fully understood effects toward debilitating the microorganisms. A few microseconds later and while the magnetic field gradient is being directed within the volumetric region, an electrohydraulic discharge is effected between a plurality of electrodes 20 for generating the lethal electrohydraulic discharge within the magnetic field envelope to kill the microorganisms, without requiring a closed, thick-walled vessel with high structural strength to contain the electrohydraulic discharge.

Considering the apparatus in more detail, the nonmagnetic, nonconductive flow conduit 13 may be a conventional plastic pipe, or any other nonmagnetic, nonconductive conduit through which the liquid-like substance may be flowed. The flow means illustrated by pump means 15 may be of conventional construction. It will be connected on its inlet side via a conduit 23 with a tank 25 containing the liquid-like substance such as raw or partially digested sewage 27 containing the microorganisms to be killed. The pump means 15 is connected via conduit 17 at its discharge with flow conduit 13, as indicated.

The magnetic field generating means 19 comprises two basic elements, the first being a magnetic field generating structure 29 and the second being a current supply means. The magnetic field generating structure 29 is illustrated as a compression coil comprising a plurality of tubular coils 33. The tubular coils 33 are formed of an electrically conductive material such as copper. They have a coolant 35 such as water flowing therethrough for dissipation of heat generated by the high currents, the high magnetic fields and the high magnetic flux densities to which they will be subjected. The plurality of tubular coils 33 may comprise a singular tube traversing through a plurality of encircling coils such that the electrical current will flow serially through the tube. It is preferable, however, if the tubular coils are connected in parallel with each other and in series with one major electrical bus 37 and a second major electrical bus 39 in order to carry the largest possible current with the least impedance and thereby generate more intense magnetic fields and magnetic field gradients for containing and directing the electrohydraulic discharge, and in a specific aspect for ensuring complete kill of the microorganisms.

Another embodiment of the compression coil disposed about conduit 13 for generating a magnetic field is illustrated in FIGS. 2 and 3. Therein, the compression coil for generating the magnetic field comprises a plurality of discs, or wafers, 69 electrically connected in parallel with each other and in series with the major electrical buses 37 and 39. The electrical buses 37 and 39 are connected, respectively, with conductors 55 and 57 of the current supply means which is described hereinafter. The annular discs 69 are formed of a conductive material such as copper. The discs 69 have an annular plate section that may be from 3 to 5 inches wide and a thickness of from $\frac{1}{4}$- to $\frac{3}{4}$-inch. A coolant 35 such as water flows between the discs. Specifically, the water may flow in through inlet conduit 71 and out through effluent conduit 73. The heat absorbed by the coolant will be dissipated in a suitable means such as a cooling tower (not shown). Advantageously, the coolant circulates in a once through flow pattern in which it will enter into a header chamber 75 (FIG. 3), flow intermediate the respective discs 69 and exit via effluent header chamber 77. The same sort of header chamber structure may be advantageously employed in the construction illustrated in FIG. 1. In the construction of FIG. 1, the header chamber wall to which the plurality of coils 33 are connected in sealing relationship, may also serve as the electrical buses 37 and 39.

As can be seen from FIGS. 1–3, the magnetic lines of force 79 converge toward the center of the flow conduit 13 to generate extremely high field intensities and field gradients for at least confining and directing the electrohydraulic discharge, as described hereinafter.

Referring back to FIG. 1, the current supply means 31 comprises a capacitive element such as capacitor 41 and a charging means 43. The charging means 43 may include its own power source or may be connected with an external power source such as power source 45. The charging means 43 is electrically connectable via conductors 47, 49 and first switch means 51 with capacitor 41. Capacitor 41 is electrically connectable with the compression coil via a second switch means 53 and conductors 55 and 57. The charging means 43 may include a transformer or other element capable of charging capacitor 41 to the desired voltage. The charging means 43 may employ, as its power source 45, pulsating direct current or alternating current which is ordinarily connected to the primary coil of the transformer (not shown). Such charging means are well known in the prior art and need not be described herein. The first switch means 51 may comprise any satisfactory electrical switch commensurate with the output from the charging means 43 and the capacitance of the capacitor 41. Suitable current limiting resistors (not shown) may be employed to prevent large current surges during the initial charging of the capacitor 41. The capacitor 41 will have a large capacitance to enable dumping of high current through the magnetic field generating structure 29 upon closure of the second switch means 53. The second switch means 53 will require a switch capable of sustaining very high current flow without damage. Typical of such switches are the ignitrons, or other mercury vapor switches, or gaps that conduct at predetermined voltages.

The electrohydraulic discharge means embodies, in addition to the plurality of electrodes 20, a current supply means 59 which includes a capacitive element such as capacitor 61 and a charging means 63. As with charging means 43, the charging means 63 may include its own power supply or may be connected with an external power source such as power source 65. The charging means 63 is electrically connectable via conductors 81 and 83 and third switch means 85 with the capacitor 61. The capacitor 61 is electrically connectable with the electrodes 20 via fourth switch means 87 and conductors 89 and 91. The charging means 63, also, may include a transformer or other element capable of charging the capacitor 61 to the desired voltage. The third switch means 85 may comprise any satisfactory electrical switch commensurate with the output from the charging means 63 and the capacitance of the capacitor 61. Suitable current limiting resistors (not shown) may be employed to prevent large current surges during the initial charging of the capacitor 61. The capacitor 61 will have a large capacitance to enable dumping of a high current through the electrodes 20 upon closure of the fourth switch means 87 for generating an electrohydraulic discharge of high power and intensity. Accordingly, the fourth switch means 87 will require a switch capable of sustaining very high current flow without damage. Typical of such switches are the ignitrons, or other mercury vapor switches.

Figure 5:
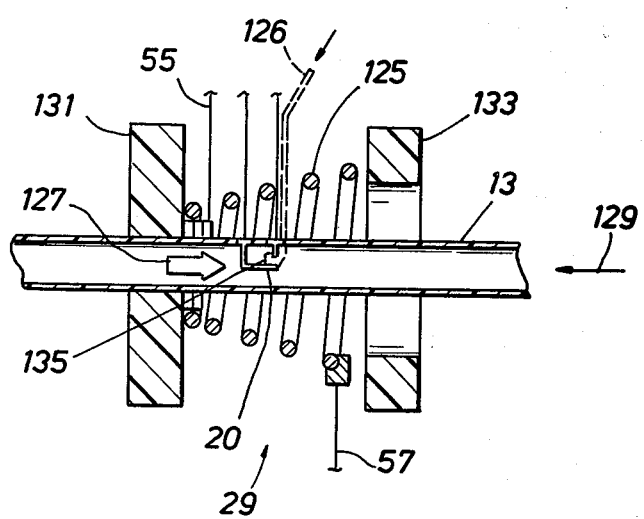
FIG. 5 is a side elevational view, partly in section, illustrating another embodiment of this invention in which the magnetic field generating structure generates a parabolic magnetic field.

The cycle control means 21 is operably connected with the first switch means 51 via suitable means 93, with second switch means 53 via suitable means 95, with third switch means 85 via suitable means 97, and with fourth switch means 87 via suitable means 99. By "suitable means", it is meant an interconnection appropriate to the type of switch means selected. For example, suitable means 93 and 97 may be an electrical connection with an electronic switch, such as an FET (fluid effect transistor) or an SCR (silicon controlled rectifier), employed as the first and third switch means 51 and 85. Similarly, the suitable means 95 and 99 may be an electrical connection with an ignitron to effect current flow via the mercury vapor therein. The cycle control means 21 is connected with the respective switches so as to effect periodic and inverse operation of the first and second switch means 51 and 53, and to effect periodic and inverse operation of the third and fourth switch means 85 and 87. In addition, the cycle control means 21 is operably connected with the second and fourth switch means 53 and 87 so as to effect conjoint generation of the physical magnetic field and the electrohydraulic discharge. Preferably, the cycle control means 21 will effect closure of second switch means 53 a few microseconds before it effects closure of fourth switch means 87. This may be effected by an internal delay means such as delay line within the cycle control means 21. Alternatively, as illustrated in FIG. 5, the delay means may be incorporated into the circuit on the exterior of the cycle control means 21. If desired, elaborate and individual controls may be employed to effect operation of the respective switches. Ordinarily, however, a simple frequency adjustment, illustrated by rheostat knob 101, may be employed for adjusting the repetition rate at which the respective capacitors 41 and 61 are discharged through, respectively, the magnetic field generating structure 29 and the electrohydraulic electrodes 20. For example, the cycle control means 21 may include any of the conventional timers, such as the electronic timers employing an RC network and means for charging the timing capacitor of the RC network, with means, indicated by rheostat knob 101, for altering the resistance and hence, the interval of time it takes to charge the timing capacitor to the requisite voltage, and a means such as a unijunction transistor for firing the timing capacitor to generate a periodic pulse which can be employed by conventional electrical and electronic means to effect the respective operations of the switch means 51 and 53, and 85 and 86, as described above. The details of such timing equipment do not per se form a part of this invention and need not be described herein, since they are well known.

Operation

In operation, the charging means 43 and the charging means 63 are connected with their respective power sources 45 and 65 by closure of the first and third switch means 51 and 85 to begin charging the capacitors 41 and 61. The cycle control means 21 is adjusted to effect a desired repetition rate by turning rheostat knob 101. As indicated, the repetition rate is such that every differential volume of the liquid-like substance to be treated will be subjected to at least one lethal electrohydraulic discharge and one pulsed magnetic field and is, consequently, proportional to the rate of flow of liquid effected by the pump means 15. Concommitantly, the pump means 15 is started to pump the sewage through the flow conduit 13.

The cycle control means 21 opens first and third switch means 51 and 85. The cycle control means 21 closes second switch means 53 to discharge the accumulated charge on the capacitor 41 through the magnetic field generating structure 29 to produce an intense magnetic field that is passed into the sewage through the flow conduit 13. A few microseconds later, by means of a delay means, the fourth switch means 87 is closed, discharging capacitor 61 through the electrohydraulic discharge electrodes 20 to produce an intense electrohydraulic discharge having a wave front that is as nearly infinite as practical in its slope of magnitude versus distance in the direction of movement and that is lethal to the microorganisms in the sewage. The compressing magnetic field generated by the magnetic field generating structure 29, envelops and contains the electrohydraulic discharge, protecting the walls of the flow conduit 13 from the intense power effected by the electrohydraulic discharge. The organisms in the sewage are subjected to both the electrohydraulic discharge and the magnetic field and are killed thereby.

Once the capacitors 41 and 61 are discharged, the cycle control means effects opening of the second and fourth switch means 53 and 87, and closure of the first and third switch means 51 and 85 to commence charging the capacitors 41 and 61 again. The first and third switch means 51 and 85 and the second and fourth switch means 53 and 87 are switched conjointly as pairs and alternately and inversely with respect to each respective pair, with or without the time delay between closure of second switch means 53 and fourth switch means 87, to generate and pass the electrohydraulic discharge and the physical magnetic field periodically through the volumetric region defined by the flow conduit 13 at the predetermined repetition rate, as indicated above and described in more detail under the General Considerations.

Once one skilled in the art is made aware of the principles of the invention, namely, separation of minerals precipitated from the solution and killing microorganisms in a liquid-like substance by treating every differential volume of the liquid-like substance with a lethal electrohydraulic discharge and physical magnetic field, whether or not of lethal intensity also, many other embodiments for effecting the results can be designed, even though they may be less satisfactory in some aspects. For example, a magnetic field generating structure may be incorporated directly into the wall of conduit 13 or even interiorly thereto. The magnetic field generating structure in this case would be subjected, together with the flow of the materials immediately therepast, directly to the effects of the electrohydraulic discharge, even though partially contained and directed by the pulsed magnetic field. Such apparatus may in fact be more desirable for extraction and separation of minerals from solution.

Other specific structures for generating the magnetic field may be useful. Such other types of structures are illustrated in FIGS. 4 and 5. In FIG. 4, a plurality of parallel connected plate structures 103 are connected via respective conductors 55 and 57, and appropriate second switch means 53 with a capacitor 41 (as illustrated in FIG. 1) for producing a magnetic field that is linear along the longitudinal axis of the flow conduit 13. Preferably, there are opposing sets of parallel connected plate structures such as plate structures 103 and 105 for passing the physical magnetic field compressively through the liquid being flowed through the nonmagnetic, nonconductive conduit 13. As illustrated, the nonmagnetic, nonconductive conduit 13 is rectangular in cross section to achieve a more nearly uniform flux gradient through the liquid-like substance being passed therethrough. As with the other embodiments, a coolant 35 is flowed intermediate the plates 103 and 105 for dissipating the heat generated by the high current flow and the magnetic flux therethrough. The coolant may be flowed in through inlet conduits 71 and out through effluent conduits 73.

FIG. 5 illustrates another embodiment in which the magnetic field is shaped by the magnetic field generating structure 29 to contain and direct the electrohydraulic discharge. Specifically, the coils 125 of the magnetic field generating structure 29 are positioned so as to generate a parabolic magnetic field that will be directed in the direction of arrow 127 toward the incoming untreated sewage, indicated by arrow 129. The electrohydraulic electrodes 20 serve for generating the electrohydraulic discharge within the parabolic pulsed magnetic field. Suitable base insulator block 131 and suitable insulated directional block such as block 133 serve to enhance the parabolic directivity of the parabolic magnetic field such that it contains the electrohydraulic discharge and directs its main force and shock wave in the direction indicated by arrow 127. The coils 125 are connected with respective conductors 55 and 57 and otherwise operate as described above. If desired, an initiating means such as an initiating filament 135 may be employed in conjunction with the electrohydraulic electrodes 20 for initiating the desired intensity electrohydraulic discharge. The initiating means may be a solid ribbon, a shaped wire, a smaller gap between secondary electrodes, or even a gaseous discharge, such as from nozzle 126 shown in dashed lines in FIG. 5 across the electrohydraulic electrodes. The gas employed in a gaseous discharge initiating means may be a gas such as chlorine that is also toxic to the microorganisms, particularly when the gas is ionized by the electrohydraulic discharge. Such toxic gas initiating means further ensures complete kill.

Even more tremendous temperatures and pressures may be effected by incorporating expendable elements, such as magnetic field generating coils 125 and the electrohydraulic electrodes 20, within the nonmagnetic and nonconductive conduit 13. Both the magnetic field envelope and the electrohydraulic discharge, timed as indicated above, contribute to the tremendous temperatures and pressures. The temperatures and pressures are so great that both the elements comprising the expendable magnetic field generating coils and the electrohydraulic electrodes are destroyed. The premanufactured elements are accordingly replenished, after each generation of the respective magnetic field and the electrohydraulic discharge, by a conventional repetitive feeding means through appropriate entry points to within the conduit 13. Despite the tremendous pressures and temperatures of hundreds of thousands of atmospheres and degrees Fahrenheit is localized regions, the conduit 13 is not required to be structurally strong since the magnetic envelope encloses and contains the electrohydraulic discharge. Expressed otherwise, the inwardly moving physical magnetic field contains and opposes the force of the outward moving shock wave and ionized particles from the electrohydraulic discharge. Both cooperate to produce the extremely high temperatures and pressures in the center, however. When coil 125 is expendable, it is replenished intermediate the electrodes at the terminals of conductors 55 and 57. Ordinarily, it will not be necessary to employ an expendable coil but merely to shape the coils which will be employed to generate the shaped magnetic field.

In the embodiments illustrated above, the electrohydraulic discharge electrodes 20 have been illustrated schematically as conventional electrodes positionable within the flow conduit 13 in communication with the substance flowing therepast. An improved electrode structure is illustrated in cross section in FIG. 6.

Referring to FIG. 6, the electrodes 20 comprise linear electrodes of an erosion resistant metallurgical construction. A particularly preferred composition of such electrodes comprises 68–71% by weight tungsten, 5–8% by weight carbon, about 12% by weight cobalt, and about 12% by weight titanium. Basically, the improved electrode structure comprises a first insert member 107 and an interiorly protruding arm means 109 carrying one of the electrodes 20. Both the first insert member 107 and the arm means 109 are electrically conductive. The first insert member 107 is connected with one of the conductors such as conductor 89 from the capacitor 61. A second one of the electrodes 20 is sealingly retained and concentrically disposed within the first insert member 107. It is connected via a bus 111 with the other conductor 91 from the capacitor 41. The bus 111 may be of copper alloy or another suitable electrical conductor. An insulating means such as polypropylene sleeve 113 is disposed intermediate the second electrode 20 and the first insert member 107, or more specifically, a bushing 115 within the first insert member 107. The bushing 115 and the polypropylene sleeve 13 may be formed with threaded connection therebetween to resist being separated under the high energy of the electrohydraulic discharge and to permit adjusting the gap between the electrodes. The bushing 115 may be suitably affixed, as by threaded connection, within the first insert member 107. A suitable means such as bolts and threaded apertures 117 and 119 are provided for sealingly retaining the first insert member 107 within the nonmagnetic conduit 13 defining the volumetric region. Suitable insulator 121 may be employed intermediate the respective conductive components, but ordinarily is not necessary with the nonmagnetic, nonconductive means employed herein to define the volumetric region. A seal means such as O-ring 123 is employed to prevent leaking about the first insert member 107 and any insulation employed in conjunction therewith.

With this construction, the force of the electrohydraulic discharge acts on the arm means 109 to partially counteract the force acting on the first insert member 107 tending to blow it outwardly from the flow conduit 13, or other nonmagnetic, nonconductive member defining the volumetric region. If desired, the bushing 115 may be interiorly threaded, as indicated, such that the bottom electrode 20 can be screwed upwardly to obtain the proper separation or gap between the electrodes.

Figure 7:
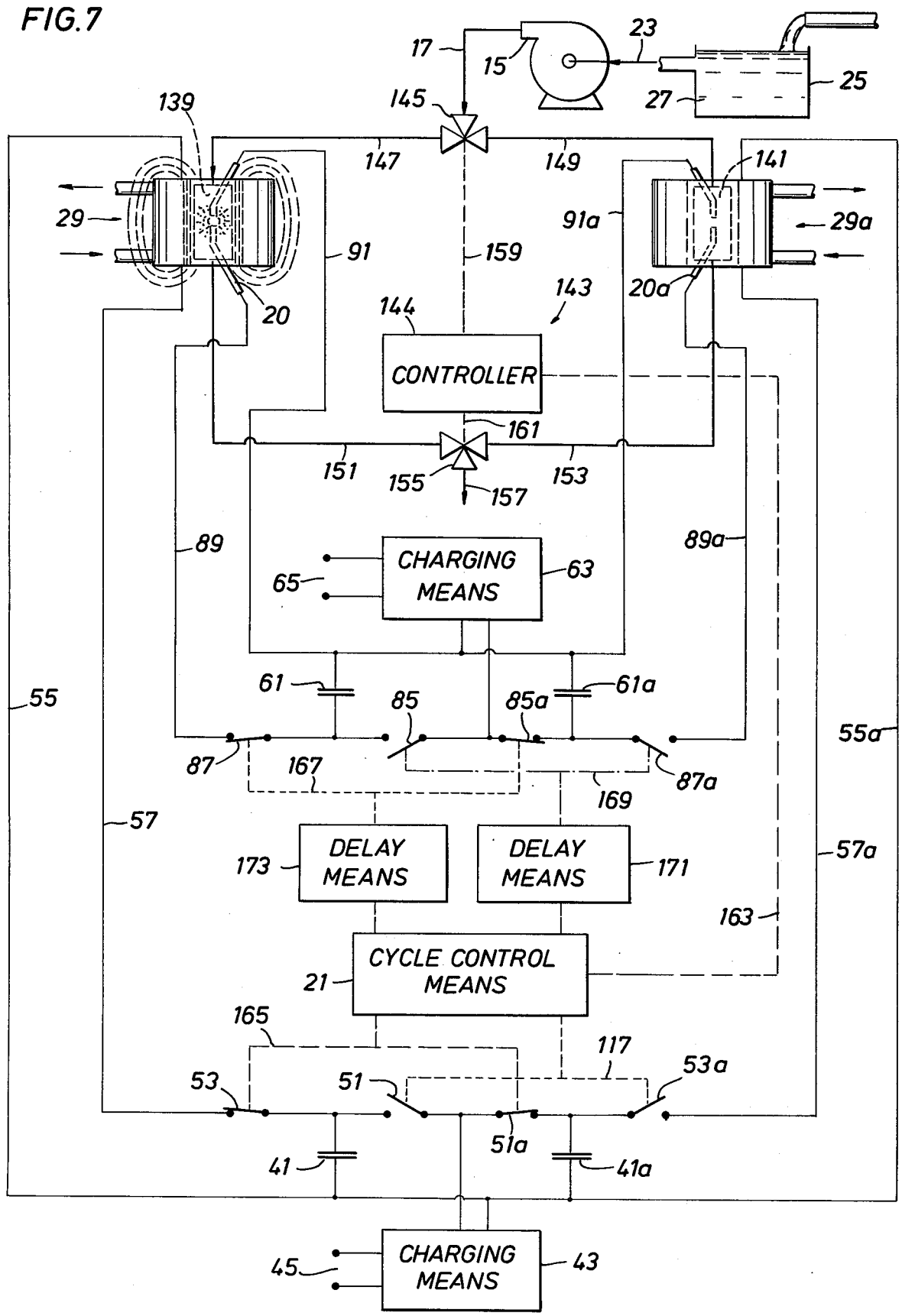
FIG. 7 is a schematic illustration of an apparatus that may be employed in either a batch, or a modified batch-continuous type of treatment, in accordance with another embodiment of this invention.

FIG. 7 illustrates schematically another embodiment for operation of the invention in a batch or modified batch-continuous process. Therein, the nonmagnetic, nonconductive means defining the volumetric region for receiving the liquid-like substance comprises nonmagnetic and nonconductive residence chambers 139 and 141 which are disposed within magnetic field generating structures 29 and 29a. The flow means comprises the pump means 15 and a control means 143. The control means 143 will effect filling of a residence chamber such as chamber 139 and, after a lethal electrohydraulic discharge and magnetic field have been passed therethrough, will effect emptying of the residence chamber 139 to effect a batch flow and treatment of the liquid-like substance. As illustrated, the control means includes a controller 144 and a plurality of multiple-way valves for sequentially and inversely filling and emptying a plurality of residence chambers 139 and 141 for effecting a modified batch-continuous flow and treatment of the liquid-like substance, the apparatus effecting a passage of the lethal electrohydraulic discharge and accompanying magnetic field through each respective chamber between the time it is filled and the time it is emptied or partially emptied.

Specifically, pump means 15 is connected at its inlet via conduit 23 with a suitable source of the liquid-like substance, such as tank 25 containing sewage 27. The pump means 15 also has its discharge connected via conduit 17 with three-way valve 145. The three-way valve 145 has its respective effluent ports connected via conduit 147 with residence chamber 139 and via conduit 149 with residence chamber 141. The discharge side of the residence chambers 139 and 141 are connected via respective conduits 151 and 153 with the intake ports of three-way valve 155. The three-way valve 155 is connected via its discharge port with a suitable disposal line 157. The disposal line 157 may lead to a lake or river since the microorganisms will have been killed in the sewage, and consequently, there will be no biological oxygen demand made on the stream or lake receiving the discharged, treated sewage. Also, the treated mineral water can be released into the surface water since the minerals and salts have been removed totally or in sufficient quantity so as not to present a hazard to the environment.

The control means 143 also includes control lines 159 and 161 connecting respectively with the three-way valves 145 and 155. Both three-way valves 145 and 155 are correlatively positioned to effect flow through either residence chamber 139 or 141 after the electrohydraulic discharge and the magnetic field have been passed therethrough. The controller 144 may include a conventional timer connected with a pneumatic source so as to effect a pneumatic signal effecting the respective positioning of the three-way valves, or it may be an electronic source employing logic elements in an arrangement such as ring counter, with or without a timer to effect the cyclical and inverse filling, passing of the electrohydraulic discharge and magnetic wave therethrough, and emptying, or partial emptying, of the respective residence chambers.

Preferably, the controller 144 has an interconnection indicated by dashed line 163 with the cycle control means 21 so as to effect the passage of a magnetic field into an electrohydraulic discharge within the residence chamber just filled and before the chamber is emptied. Such interconnection is not absolutely necessary, however, since the control cycle means 21 may have a separately controllable repetition rate such as described above with respect to rheostat knob 101 for controlling the repetition rate at a frequency great enough to ensure that every differential volume of the sewage in the respective residence chambers has a physical magnetic field and an electrohydraulic discharge of lethal intensity passed therethrough at least once. The incterconnection ordinarily will allow a lower repetition rate in response to the flow rate.

It is not necessary that a residence chamber be completely emptied and the opposite one completely filled each time the three-way valves are switched. For example, if it is desired that each differential volume receive two passages of the lethal electrohydraulic discharge and the magnetic field therethrough, the three-way valves may be switched when the containers are only half emptied of the treated sewage. Similarly if three passages of the electrohydraulic discharge and the magnetic field are desired, the switching of the three-way valves 145 and 155 may be effected at a rate such that the residence chambers are only one-third emptied of treated sewage.

In any event, the cycle control means 21 effects the generation and passage of a magnetic field into and the electrohydraulic discharge within the respective residence chambers via closure of the respective switches in the manner delineated above. Specifically, when one capacitor 41 or 41a is being discharged through a closed switch means 53 or 53a to generate and pass the magnetic field into the respective associated residence chamber, the opposite switch means 51a or 51 is closed to charge the opposite capacitor from the charging means 43. The cycle control means 21 effects concomitant closing or opening of the switch means 53 and 51a, indicated by dashed line 165, and effects concomitant and inverse opening or closing of switch means 51 and 53a, indicated by dotted line 117. The concomitant operation is not vital, since the switches may be individually controlled as desired to effect the described frequency and intensity of the pulsed magnetic fields.

Conjointly with the generation of the magnetic field, cycle control means 21 effects, via closure of either fourth switch means 87 or 87a, generation of the electrohydraulic discharge at the respective pair of electrodes 20 or 20a associated with the magnetic field generating structure in the manner delineated above. When one capacitor 61 or 61a is being discharged through a closed switch means 87 or 87a to generate the electrohydraulic discharge within a respective residence chamber and within a respective magnetic field, the opposite switch means 85a or 85 is closed to charge the opposite capacitor from the charging means 43. The cycle control means 21 effects concomitant closing or opening of the switch means 87 and 85a, indicated by dotted line 167, and effects concomitant and inverse opening or closing of switch means 85 and 87a, indicated by dashed line 169. Again, the concomitant operation is not vital, since the switch means may be individually controlled as desired to effect the described frequency and intensity of the electrohydraulic discharge. It is vital however, as indicated above that the electrohydraulic discharge be effected conjointly with the magnetic field such that the electrohydraulic discharge occurs within the magnetic field envelope. Preferably, as indicated above, the generation of the magnetic field is initiated a few microseconds in advance of the electrohydraulic discharge. Accordingly, the signals from the cycle control means 21 may be sent via appropriate delay means 171 or 173 for effecting the few microseconds delay of electrohydraulic discharge. Any other arrangement that will effect the conjoint generation of the magnetic field and the electrohydraulic discharge may be emloyed.

Preferably, the cycle control means 21 employs a pneumatic or logic system that is compatible with the controller 144 when there is an interconnection therebetween. This simplifies correlative operation between the respective three-way valves, and the respective current generating means for pulsing the respective magnetic field generating structures 29 or 29a and the electrohydraulic electrodes 20 or 20a associated with the respective residence chambers 139 and 141.

The respective magnetic field generating structures are electrically connected with their respective capacitors and have the respective flow of coolant therethrough as described above. The electrohydraulic electrodes are also connected with their respective capacitors as described above.

In operation, the pump means 15 will pump sewage 27 via flow passageway through three-way valve 145 into conduit 149 and residence chamber 141. Simultaneously, three-way valve 155 will allow treated sewage to flow via conduit 153 from the residence chamber 141 to prevent liquid blocking. During this interval, the cycle control means 21 will effect closure of switch means 53 and 51a, and after a short delay, closure of switch means 87 and 85a. The closed switch means 51a and 85a initiate the charging of capacitors 41a and 61a. Switch means 53 effects discharge of capacitor 41 via conductors 55 and 57 through the magnetic field generating structure 29, generating the magnetic lines of flux 79 and passing the magnetic field compressively into the residence chamber 139 and the sewage therein. A few microseconds later, switch means 87 closes and discharges capacitor 61 through the electrohydraulic electrodes 20, generating the lethal electrohydraulic discharge within the residence chamber 139 and within the magnetic field generated by magnetic field generating structure 29. The microorganisms within the sewage in residence chamber 139 are killed.

The controller 144 then effects, via suitable means such as flip-flop oscillator or ring counter, switching of the three-way valves 145 and 155 to block the flow from residence chamber 141 and flowing of the sewage into the residence chamber 139 and flowing of the treated sewage therefrom. The cycle control means 21 opens switch means 53 and 51a and closes switch means 51 and 53a. After the appropriate few microseconds delay, the cycle control means 21 also opens switch means 87 and 85a and closes switch means 85 and 87a. The switch means 51 and 85 effects recharging of the capacitors 41 and 61. The switch 53a effects discharge of the capacitor 41a through the magnetic field generating structure 29a to pass the magnetic field into the residence chamber 141. The switch means 87a discharges the capacitor 61a across the electrohydraulic electrodes 20a to generate the lethal electrohydraulic discharge within the residence chamber 141 and within the magnetic field. After passage of the lethal electrohydraulic discharge and the magnetic field through the sewage in residence chamber 141, the control means 143 again effects operation of the three-way valves to flow untreated sewage into and treated sewage from the residence chamber 141 to repeat the cycle described immediately above.

More than two residence chambers may be employed and the control means 143 may employ a ring counter with the same number of operative logic elements to sequentially effect filling, treatment, and emptying or partial emptying of each of the residence chambers. Ordinarily, it will be advantageous to employ a capacitor such as capacitor 41 and a respective magnetic field generating structure and respective electrodes for each of the residence chambers. It may be necessary to employ a plurality of charging means to effect the requisite charging of the plurality of capacitors.

Figure 8:
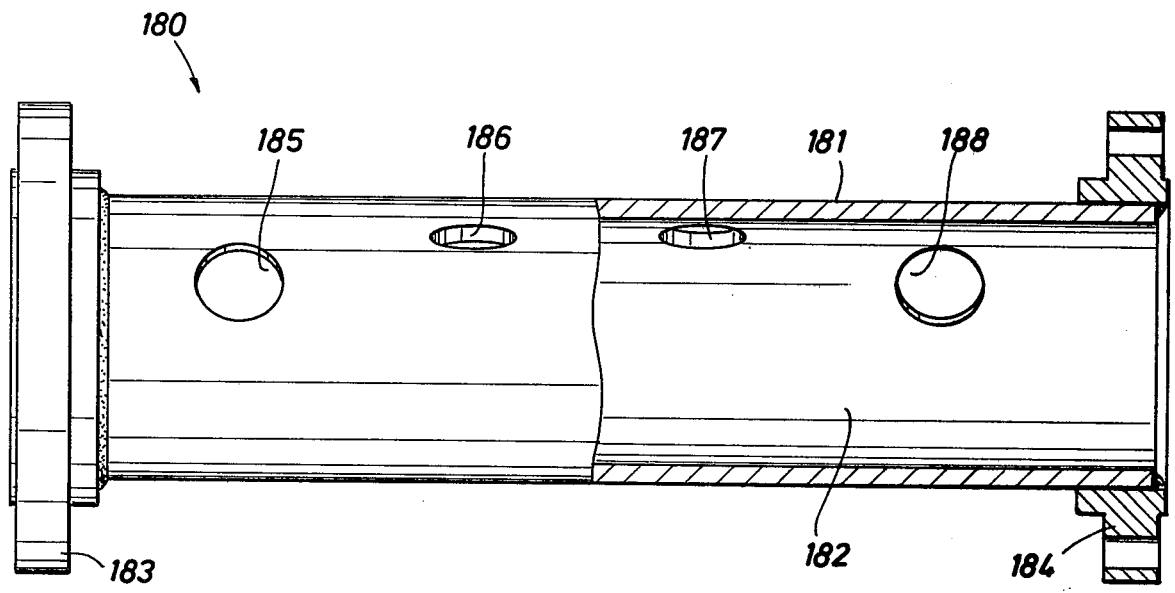
FIG. 8 is a partial sectional view of a discharge chamber illustrating serpentine positioning of electrode openings which receive ignition electrodes surrounding the firing chamber.
Figure 9:
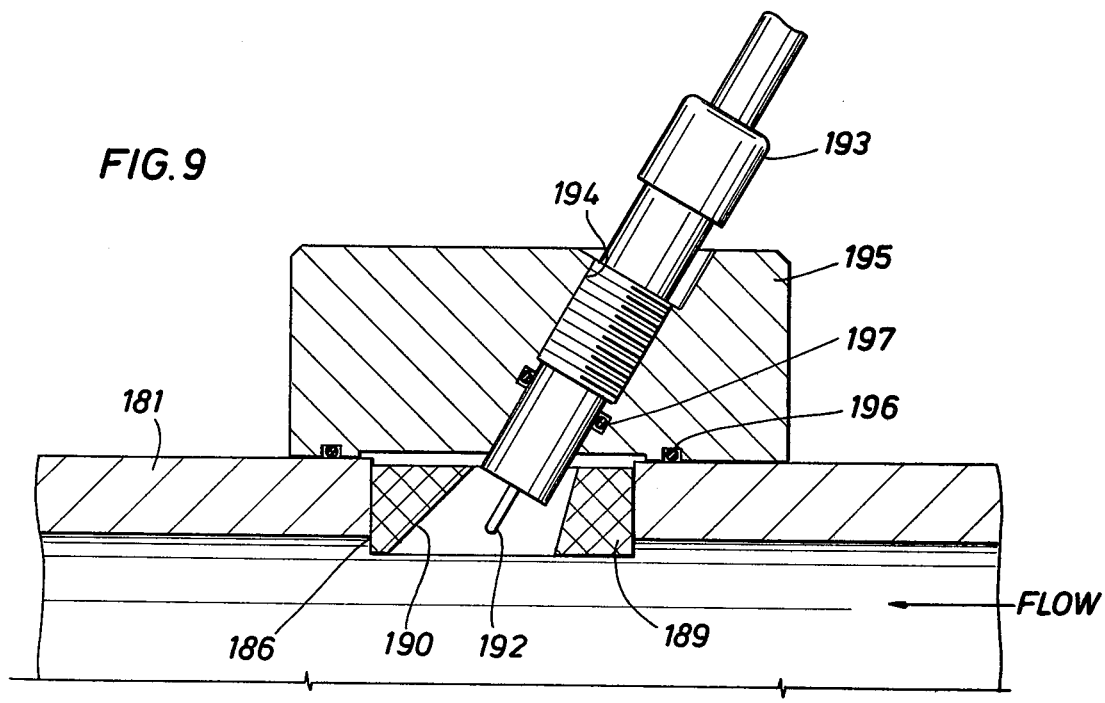
FIG. 9 is a fragmentary sectional view of the discharge and firing chamber of FIG. 8 and illustrating the angular orientation of the ignition spark plug relative to the firing chamber.

Referring now to FIGS. 8 and 9, a discharge chamber or firing chamber is illustrated generally at 180 which incorporates an elongated tubular element 181 defining a flow passage 182. Connection flanges 183 and 184 are provided at each extremity of the conduit element 181.

In order to provide for efficient discharge into the flow passage or discharge chamber 182, ignitron devices are positioned at diverse locations about the tubular element 181. As shown, apertures are positioned in a serpentine pattern as shown at 185, 186, 187 and 188. As shown in the fragmentary sectional view of FIG. 9, aperture 186 is provided with an interfitting coil 189 which defines an inclined, tapered discharge passage 190 within which is positioned the spark gap element 192 of an ignitron spark plug 193. Spark plug 193 is received within a threaded opening 194 of a housing 195 which surrounds the tubular element 181. The housing is sealed with respect to the conduit 181 by means of circular sealing element such as an O-ring or the like as shown at 196. The ignitron spark plug is sealed with respect to the housing 195 by means of a circular sealing element 197.

By positioning the ignitron spark plug in an inclined position, its electrical discharge is inclined with respect to the direction of fluid flow through the continuous flow passage 182 of the firing chamber. Each of the ignitrons will be similarly positioned in inclined relation with respect to the direction of fluid flow such that the axis of the spark plug is direct downstream. As the spark plug discharges, the resulting electrohydraulic shock that is developed forms a shock wave in the fluid which is oriented in the downstream direction by virtue of the inwardly flared surface 190 of the coil 189.

The ignitron apertures 185-188 are positioned in spaced relation with spacing such that cavitation from an electrohydraulic discharge will have dissipated prior to the time the flowing fluid reaches the next successive downstream ignitron. In the case of rapidly flowing fluid therefore, the spacing of the ignitrons must be greater than in a similar firing chamber where fluid will flow at lower velocity. Such ignitron spacing is necessary in order to prevent electrical discharge into a cavitation which has not yet collapsed from a previous upstream discharge. Otherwise, the electrohydraulic shock effect of the discharge will not achieve its maximum viability.

General Considerations

The following general considerations should be borne in mind with respect to employing this invention. The phenomena of the electrohydraulic discharge and its effect on the microorganisms is not fully understood. The following theory is given in explanation and not in limitation of this invention.

The spark gap arc across the electrohydraulic electrodes releases a large quantity of energy in a small area to effect localized temperatures of many thousands of degress, instantaneously vaporizing and ionizing everything within the arc. Many thousands of atmospheres of over pressure are created locally and a sharp shock wave is generated. As indicated above, it is known that the shock wave accompanying the electrohydraulic discharge has a more nearly inifnite slope in liquids. The liquids must have some conductivity and the greater the conductivity, the more nearly infinite the slope of the shock wave beocmes. The shock wave from an electrohydraulic discharge is known to have great power, for example, sufficient to deform metals, and it is lethal to the small organisms. In addition to the lethal effects of the shock wave, however, there is an accompanying emission of ultraviolet light and photons, free radicals and a production of ozone, all of which provide effects which are lethal to the microorganisms. The exact power and intensity of an electrohydraulic discharge sufficient to be lethal to the particular microorganism has not been completely delineated for every variety. It is known that even small electrohydraulic discharges such as effected by capacitances of only about 0.1 microfarad at about 6,000 volts, produce over pressures of more than 1,000 atmospheres at a distance of about one centimeter from the electrohydraulic discharges. The greater the voltage and the greater the current flowing during the electrohydraulic discharge, the greater the power. For example, as indicated above, some electrohydraulic discharges require extremely strong vessels to confine the liquid in which the electrohydraulic discharge is produced. The current effected by the electrohydraulic discharge and consequently, the power, will be proportional to the capacitance of the capacitor that is discharged. The capacitors such as capacitor 61 should have a capacitance of at least 0.1 microfarad, and preferably on the order of 10-100 microfarads, or even higher. The capacitors should be charged to a voltage of at least 3,000 volts and preferably between 4,000 and 8,000 volts to effect the desired power of the electrohydraulic discharge. The voltages are desirably kept below corona discharge voltages of 30,000 volts and higher. Suitable circuits for effecting the desired charging of the capacitor and the switching between the charging means and the electrodes with respect to the capacitor are known and need not be described in detail herein.

The gap between the electrohydraulic electrodes may be adjusted for, inter alia, the power and intensity of the discharge desired for a given application and for the liquid-like substance to be treated. Ordinarily, at least 12 millimeters separation should be effected between the electrodes to achieve a suitable electrohydraulic discharge. Larger gaps may be employed with high voltage discharges, particularly in relatively conductive liquid-like substances. Gaps up to 45-50 millimeters may be employed. With initiation filaments, gaps up to 100 millimeters or even larger may be employed.

The magnetic field must have an intensity sufficient to contain and direct the electrohydraulic discharge to prevent deformation of the nonmagnetic, nonconductive means defining the volumetric region through which the substance to be treated is flowed. Expressed otherwise, the magnetic field compresses the ionized, conductive particles generated by the electrohydraulic discharge and increases the lethal effect of the electrohydraulic discharge, as well as permitting the use of lighter weight construction in the nonmagnetic, nonconductive means within which the electrohydraulic discharge occurs. Desirably, the magnetic field peaks just at the instant the electrohydraulic discharge energy release does. The magnetic field is of longer duration and passes through the substance being treated unless opposed by the conductive ionized particles of the electrohydraulic discharge. The intensity of the magnetic field necessary to contain the electrohydraulic discharge will vary with the power of the electrohydraulic discharge. It is within the skill of the art to employ a variety of increasing magnetic fields to ascertain the intensity of the magnetic field necessary. One rule of thumb which is useful in this regard is to employ a power release about three to five times as great in the magnetic field generating structure as across the electrohydraulic electrodes. This may be done by choking the current flowing through the electrohydraulic electrodes or employing a lower capacitance for them. For example, the capacitance of capacitor 61 might be in the range of 10–100 microfarads and the minimum capacitance of capacitor 41 might be 4 times as great and in the range of 40–400 microfarads. Greater intensity magentic fields are beneficial, so the foregoing guidelines are minimal, as far as the magnetic fields are concerned.

Specifically, as indicated above, it is preferred that the magnetic field have an intensity sufficient to be lethal to the microorganisms present in the fluid involved. It should be borne in mind, however, that the exact threshold necessary to be lethal for every variety of microorganism has not been completely delineated.

Some typically lethal magnetic fields are expected to be about 5,000 oersteds, with a nonsteady state magnetic gradient of at least 5,000 oersteds per centimeter and preferably, greater than about 10,000 oersteds per centimeter. Magnetic field strengths of about 18,000 oersteds with gradients of more than about 15,000 oersteds per centimeter are obtainable within substances being passed within a compression coil. A field shaper such as a aluminum or beryllium copper shaper may be employed about the magnetic field generating structure to concentrate the magnetic field in a predetermined volumetric region, thereby obtaining enhanced field intensities and greater magnetic field gradient intensities. About 12 capacitors, each having from 60–120 microfarads capacitance giving a total capacitance of between 720–1440 microfarads is sufficient to effect this magnitude field. It will be apparent that lower magnitude fields may be effected with lower capacitance. The charging voltage on the capacitance elements will ordinarily run between 440 and 12,000 volts, the higher voltages generating a greater intensity magnetic field when a given capacitance element is discharged through the magnetic field generating structure 29. In employing this invention, however, lower intensity magnetic fields may be employed and still effect killing the microorganisms due to electrohydraulic discharge, the lower intensity magnetic field being employed to contain and direct the electrohydraulic discharge.

With the high capacitance of the capacitors such as capacitors 41 and 61, the repetition rate or discharge of a capacitive element through either the magnetic field generating structure and the electrohydraulic electrodes will be less than about 10 cycles or repetitions per second. For example, the practical maximum rate will be about 6 times per second for a unitary capacitor bank. Somewhere between 1 to 4 times per second will be the practical repetition rate. Frequencies greater than 10, and less that 100, cycles per second are achievable by employing staged capacitor banks with staged switches for allowing charging of the respective banks while the other respective banks are discharged through their respective elements such as the magnetic field generating structure 29 or the electrohydraulic electrodes 20. The cooling load on the magnetic field generating device will increase at the higher frequencies. With ordinary flow, the repetition rate of 1 to 4 times per second will be more than adequate. In certain batch operations employing relatively large nonmagnetic, nonconductive residence chambers it may not be necessary to generate and pass the magnetic field and the electrohydraulic shock wave through the residence chamber more often than once for a time period of several seconds, or even a minute or more.

The cycle control means 21 may comprise a plurality of individually timed switch actuation means that are slaved together with the desired time arrangement, such as timers and logic devices like ring counters. On the other hand, the cycle control means 21 may comprise a first voltage responsive device such as a unijunction transistor which will automatically trigger, or turn on and off, via a suitable circuit an ignitron serving as the second switch means 53, and if desired, via a delay means, fourth switch means 87 (FIG. 1), or their equivalent in more complex processes such as shown in FIG. 7. Similarly, switch means 51 and 85, or their equivalent may be turned off and on by a second voltage responsive device that operates inversely to the first one.

As indicated above, a wide variety of cycle control means and control means are commercially available in the art. They range from pneumatic and sealed electronic devices operable in explosive atmospheres, through mechanical apparatus employing a variety of linkage arrangements. Ordinarily, the staging of the generation of the magnetic field followed by the electrohydraulic discharge a few microseconds later, is effected more accurately by electronic means, as indicated. If desired, operation of the respective switch means may be by any of the well known techniques which are capable of delivering the current flows, as indicated.

Other structures for the electrode assembly and for the magnetic field generating structure will be developed as specific applications emerge and are within the scope of the invention.

I have found it advantageous to employ a large bank of capacitors rated up to 12,000 volts with the options of switching various proportions to either the electrohydraulic electrodes or the magnetic field generating structure, or to the charging means. As many capacitors as may be needed may be connected together to form capacitive elements illustrated generically by either capacitor 41 or 61. A single charging means is employed to charge the capacitors to a single voltage that is employed for generating both the electrohydraulic discharge and the magnetic field. Units that are individually designed for a given job will not require such flexibility and will be more economical.

From the foregoing descriptive matter and drawings, it can be seen that this invention alleviates the difficulties of the prior art apparatus and enables treating a substance in either a continuous, batch, or batch-continuous operation. Moreover, the invention enables employing the efficacious electrohydraulic discharge within a magnetic envelope to alleviate problems with rupturing the nonmagnetic, nonconductive walls defining a volumetric region through which the substance to be treated is passed. In a specific aspect, the invention provides shaped magnetic fields for containing and directing the electrohydraulic discharge and provides electrohydraulic electrodes that are resistant to erosion and wear by the electrohydraulic discharge and are incorporated in an electrode structure that alleviates problems with deformation of the electrodes or the blowing of electrodes from the line due to the power of the electrohydraulic discharge.

It is worth emphasizing that this is a basic invention and although the invention has been described with a certain degree of particularity, it is understood that the present disclosure is made only by way of example and that numerous changes in the details of construction and the combination and arrangement of parts may be resorted to without departing from the spirit and the scope of the invention.

What is claimed is:

1. Apparatus for treating a substance containing microorganisms comprising:
   a. nonmagnetic means that is also electrically nonconductive defining a volumetric region for receiving said substance;
   b. electrohydraulic discharge generating means including a plurality of electrohydraulic electrodes communicating with said volumetric region so as to be able to generate an electrohydraulic discharge within said volumetric region and pass an electrohydraulic shock wave through any substance therein; said electrohydraulic discharge generating means being capable of generating an electrohydraulic discharge of an intensity sufficient to kill said microorganisms in said substance;
   c. magnetic field generating means disposed adjacent said nonmagnetic means so as to be able to pass a physical magnetic field into said volumetric region; said magnetic field generating means being capable of generating a physical magnetic field of an intensity at least sufficient to contain and direct said electrohydraulic discharge;
   d. flow means for passing said substance through said volumetric region; and
   e. cycle control means connected with said magnetic field generating means and with said electrohydraulic discharge generating means for causing said magnetic field generating means to generate said physical magnetic field and for causing said electrohydraulic discharge generating means to generate said electrohydraulic discharge within and conjointly with said physical magnetic field at a frequency great enough to ensure that every differential volume of said substance is subjected to at least one said electrohydraulic discharge and physical magnetic field.

2. The apparatus of claim 1 wherein said magnetic field generating means is capable of generating a physical magnetic field of sufficient intensity to kill said microorganisms also.

3. The apparatus of claim 1 wherein said substance is a liquid-like substance, said nonmagnetic means comprises nonmagnetic flow conduit portion and said flow means comprises a pump means for effecting continuous flow and treatment of said liquid-like substance.

4. The apparatus of claim 1 wherein said substance is a liquid-like substance, and said nonmagnetic means comprises a nonmagnetic residence chamber and said flow means comprises a pump means and a control means for filling and emptying said nonmagnetic residence chamber for effecting a batch flow and treatment of said liquid-like substance.

5. The apparatus of claim 4 wherein there are a plurality of said nonmagnetic residence chambers and said control means is operable to periodically and sequentially effect flow of untreated liquid-like substance into and treated liquid-like substance from respective said nonmagnetic residence chambers for effecting a modified batch-continuous flow and treatment of said liquid-like substance.

6. The apparatus of claim 1 wherein said magnetic field generating means comprises a field generating structure that is electrically connectable with a current supply means.

7. The apparatus of claim 6 wherein said magnetic field generating means is adapted for generating a compression-type magnetic field.

8. The apparatus of caim 6 wherein said magnetic field generating means is adapted for generating a parabolically shaped magnetic field.

9. The apparatus of claim 6 wherein said field generating structure comprises an electrically conductive plate.

10. The apparatus of claim 9 wherein there are a plurality of parallel disposed, electrically conductive plates for generating therebetween a lineally compressive, physically lethal magnetic field.

11. The apparatus of claim 6 wherein said magnetic field generating means comprises a compression coil.

12. The apparatus of claim 11 wherein said compression coil comprises a plurality of coils and an electrically conductive tubing having a coolant flowing therethrough.

13. The apparatus of claim 12 wherein said compression coil comprises a plurality of individual coils of conductive tubing, said individual coils being electrically connected in parallel.

14. The apparatus of claim 11 wherein said compression coil comprises a plurality of electrically coupled annular discs of an electrically conductive material, said discs having a coolant flowing therebetween.

15. The apparatus of claim 6 wherein said current supply means comprises a capacitive element and a charging means; said charging means being electrically connectable with said capacitive element by first switch means; said capacitive element being electrically connectable with said compression coil by a second switch means capable of conducting high current.

16. The apparatus of claim 1 wherein said magnetic field generating means includes a magnetic field shaper for concentrating the physical magnetic field for containing and directing said electrohydraulic discharge.

17. The apparatus of claim 1 wherein said electrohydraulic discharge generating means includes a second current supply means having a second capacitive element and a charging means that is electrically connectable with said second capacitive element via conductors and a third switch means; said second capacitive element being electrically connectable with said electrohydraulic electrodes via conductors and a fourth switch means.

18. The apparatus of claim 17 wherein said electrohydraulic electrodes are comprised of 68–71 percent by weight tungsten, 5–8 percent by weight carbon, about 12 percent by weight cobalt, and about 12 percent by weight titanium.

19. The apparatus of claim 17 wherein said electrohydraulic discharge generating means includes an electrode structure comprising an electrically conductive first insert member connected with one of said conductors from said second capacitor in said second current supply means and having an interiorly protruding, electrically conductive arm means carrying a first electrode; a second electrode sealingly retained and concentrically disposed within said first insert member and connected with the other said conductor from said capacitor, insulating means intermediate said second electrode and said first insert member; and means for sealingly retaining said first insert member within said nonmagnetic means defining said volumetric region.

20. The apparatus of claim 19 wherein said first and second electrodes are comprised of 68-71 percent by weight tungsten, 5-8 percent by weight carbon, about 12 percent by weight cobalt, and about 12 percent by weight titanium.

21. The apparatus of claim 17 wherein said magnetic field generating means includes a first current supply means having a first capacitive element that is electrically connectable with a magnetic field generating structure; and said first capacitive element has at least three times the capacitance of said second capacitive element.

22. The apparatus of claim 21 wherein said first capacitive element has more than four times the capacitance of said second capacitive element.

23. The apparatus of claim 22 wherein said first capacitive element has sufficient capacitance to generate a magnetic field of intensity that is also lethal to said microorganisms.

24. The apparatus of claim 21 wherein said first capacitive element has a capacitance in the range of 0.4–1440 microfarads, and said second capacitive element has a capacitance in the range of 0.1–100 microfarads.

25. The apparatus of claim 24 wherein said first capacitive element has a capacitance of at least 40 microfarads and said second capacitive element has a capacitance of at least 10 microfarads.

26. The apparatus of claim 17 wherein said electrohydraulic electrodes are separated by a spark gap of at least 12 millimeters.

27. The apparatus of claim 26 wherein said spark gap is within the range of 12–100 millimeters.

28. The apparatus of claim 11 wherein a single charging means and a single capacitor bank operable up to 12,000 volts is employed; said capacitor bank being apportionable into two major capacitor sections for being connected separately and respectively with said charging means; each section being further apportionable into first and second capacitive elements for being electrically connected into said magnetic field generating means and said electrohydraulic discharge generating means in response to said cycle control means.

29. The apparatus of claim 1 wherein an initiating means is disposed adjacent said electrohydraulic electrode for initiating said electrohydraulic discharge.

30. The apparatus of claim 29 wherein said initiating means comprises a gaseous discharge means for discharging a gas across said electrohydraulic electrodes.

31. The apparatus of claim 29 wherein said gas is also toxic to said microorganisms.

32. Apparatus for treating a substance containing a material in an undesirable form comprising:
a. nonmagnetic means that is also electrically nonconductive defining a volumetric region for receiving said substance;
b. electrohydraulic discharge generating means including a plurality of electrohydraulic electrodes communicating with said volumetric region so as to be able to generate an electrohydraulic discharge within said volumetric region and pass an electrohydraulic shock wave through any substance therein; said electrohydraulic discharge generating means being capable of generating an electrohydraulic discharge of an intensity sufficient to alter the form of said material to a more desirable form;
c. magnetic field generating means disposed adjacent said nonmagnetic means so as to be able to pass a physical magnetic field into said volumetric region; said magnetic field generating means being capable of generating a physical magnetic field of intensity at least sufficient to contain and direct said electrohydraulic discharge;
d. flow means for passing said substance through said volumetric region; and
e. cycle control means connected with said magnetic field generating means and with said electrohydraulic discharge generating means for causing said magnetic field generating means to generate said physical magnetic field and for causing said electrohydraulic discharge generating means to generate said electrohydraulic discharge within and conjointly with said physical magnetic field at a frequency great enough to ensure that every differential volume of said substance is subjected to at least one said electrohydraulic discharge and physical magnetic field.

33. The apparatus as recited in claim 1, wherein:
a. said volumetric region is defined by passage means through which material flows; and
b. said electrohydraulic discharge generating means being oriented relative to said passage means such that shock wave developed in said material by said electrohydraulic discharge enhance the flow of material through said passage means.

34. The apparatus as recited in claim 33, wherein:
a. conduit means defines said passage means, said conduit means having a wall structure;
b. a plurality of openings being formed in spaced relation along said wall structure;
c. spark generating means being located at each of said openings and being oriented to develop a plurality of electrohydraulic discharges in said material as it flows through said passage means.

35. The apparatus as recited in claim 34, wherein:
the spacing of said openings is sufficient in relation to the velocity of material flow through said passage means that electrohydraulic discharge will not project into the cavitatin of previous discharges as the material flows through said passage means.

36. The apparatus as recited in claim 34, wherein:
said spaced openings are arranged in spiral relation in said wall structure.

37. The apparatus as recited in claim 34, wherein:
a. said openings are oriented in acute angular relation with said passage means; and
b. said spark generating means are also oriented in acute angulated relation and project an electrohydraulic discharge in angularly oriented downstream directed manner.

* * * * *